US006355239B1

(12) United States Patent
Bruder et al.

(10) Patent No.: US 6,355,239 B1
(45) Date of Patent: Mar. 12, 2002

(54) USES FOR NON-AUTOLOGOUS MESENCHYMAL STEM CELLS

(75) Inventors: Scott P. Bruder, Waltham, MA (US); Kevin R. McIntosh, Ellicott City, MD (US); Daniel R. Marshak, Lutherville, MD (US); Joseph D. Mosca, Ellicott City, MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/314,855

(22) Filed: Mar. 12, 1999

Related U.S. Application Data

(63) Continuation-in-part of application No. 09/039,127, filed on Mar. 13, 1998, now abandoned.

(51) Int. Cl.$^7$ .................. A01N 63/00; A01N 65/00; C12N 5/00; C12N 5/08
(52) U.S. Cl. .................. 424/93.1; 424/93.2; 435/325; 435/372
(58) Field of Search .................. 424/93.1; 435/325, 435/455, 2, 372; 623/16

(56) References Cited

U.S. PATENT DOCUMENTS 5,226,914 A * 7/1993 Caplan et al. ............... 623/16
5,591,625 A * 1/1997 Gerson et al. ............ 435/240.2

OTHER PUBLICATIONS

Z Nevo et al., Cell Transplantation, "The Manipulated Mesenchymal Stem Cells in Regenerated Skeletal Tissues," 1998, vol. 7, No. 1, pp. 63–70.*
IM Roitt et al., Immunology, "Transplantation and Rejection," 1993, 3rd.Ed., Chap.23, pp.23.1.*
MS Leffell et al., Handbook of Human Immunology, "DNA–based Typing of HLA for Transplantation," CRC Press,1997,Chap.13, p. 545.*
Tse, et al., "Bone Marrow–Derived Mesenchymal Stem Cells Suppress T–Cell Activation without Inducing Allogeneic Anergy," *Journal of the American Society of Hematology,* vol. 96, No. 11 (Nov. 16, 2000).
Bruder SP et al. J. Cell. Biochem. 56:283–294. 1994.*
Robinson D et al. Agents Actions Suppl 39:231–235. 1993 (abstract).*
Stiller CR et al. N Engl. J. Med. 294:978–982. 1976.*
Kissinger A J Clin. Apheresis 5:97–99. 1990 (Abstract).*
Theobald, Valerie A., et al., ""Neutral Allografts"—Lack of Allogeneic Stimulation by Cultured Human Cells Expressing MHC Class I and Class II Antigens," *Tranplantation,* vol. 55, No. 1, pp. 128–133 (1993).
Goodman, et al., "Fludarabine Phosphate: A DNA Synthesis Inhibitior with Potent Immunosuppressive Activity and Minimal Clinical Toxicity," *The American Surgeon,* 62(6);435–442 (1996).

* cited by examiner

*Primary Examiner*—Dave T. Nguyen
*Assistant Examiner*—Ram R. Shukla
(74) *Attorney, Agent, or Firm*—Elliot M. Olstein; Alan J. Grant

(57) ABSTRACT

Methods and devices using non-autologous mesenchymal stem cells comprising treating a recipient in need thereof with an effective amount of non-autologous mesenchymal stem cells, including methods and preparations for treating and regenerating connective tissue and enhancing bone marrow engraftment in an individual; and for using genetically engineered allogeneic human mesenchymal stem cells that carry within them genes of interest particularly for the expression of physiologically or pharmacologically active proteins in gene therapy for correction of genetic disorders or "rebuilding" proteins important in tissue repair.

12 Claims, 9 Drawing Sheets

USES FOR NON-AUTOLOGOUS MESENCHYMAL STEM CELLS

This application is a continuation-in-part of and claims priority of U.S. patent application Ser. No. 09/039,127 filed Mar. 13, 1998 (abandoned).

The present invention is directed to various methods and products for using mesenchymal stem cells (MSCs).

In accordance with an aspect of the present invention, an animal is treated with mesenchymal stem cells wherein the mesenchymal stem cells are obtained from an animal other than the animal being treated, i.e. the mesenchymal stem cells are not autologous.

More particularly, in accordance with an aspect of the invention, a patient is treated with allogeneic human mesenchymal stem cells. As the term is used herein, an allogeneic human mesenchymal stem cell is a mesenchymal stem cell obtained from a human other than the intended recipient of the mesenchymal stem cells.

Although the mesenchymal stem cells express surface MHC molecules, applicants have found that the mesenchymal stem cells are immunologically neutral and therefore can be used as described herein without inducing an adverse immune response in the recipient of the cells.

In addition, applicants have found that the donor of the mesenchymal stem cells need not be "matched" to the recipient.

In accordance with the present invention, it has been discovered that mesenchymal stem cells are "invisible" to the immune system. Normally, co-culturing cells from different individuals (allogeneic cells) results in T cell proliferation, manifested as a mixed lymphocyte reaction (MLR). However, when human mesenchymal stem cells are contacted with allogeneic T lymphocytes, in vitro, they do not generate an immune response by the T cells, i.e., the T cells do not proliferate, indicating that T cells are not responsive to mismatched mesenchymal stem cells. This discovery was unexpected because human mesenchymal stem cells express all of the surface molecules that render them immunogenic, i.e., they express allogeneic class I and class II MHC molecules.

It has also been discovered that mesenchymal stem cells actively reduce the allogeneic T cell response in mixed lymphocyte reactions in a dose dependent manner. It has further been discovered that mesenchymal stem cells from different donors do not exhibit specificity of reduced response with regard to MHC type. Thus, mesenchymal stem cells need not be MHC matched to a target cell population in the mixed lymphocyte reaction in order to reduce the proliferative response of alloreactive T cells to mesenchymal stem cells.

DETAILED DESCRIPTION OF THE INVENTION

Figure 1:
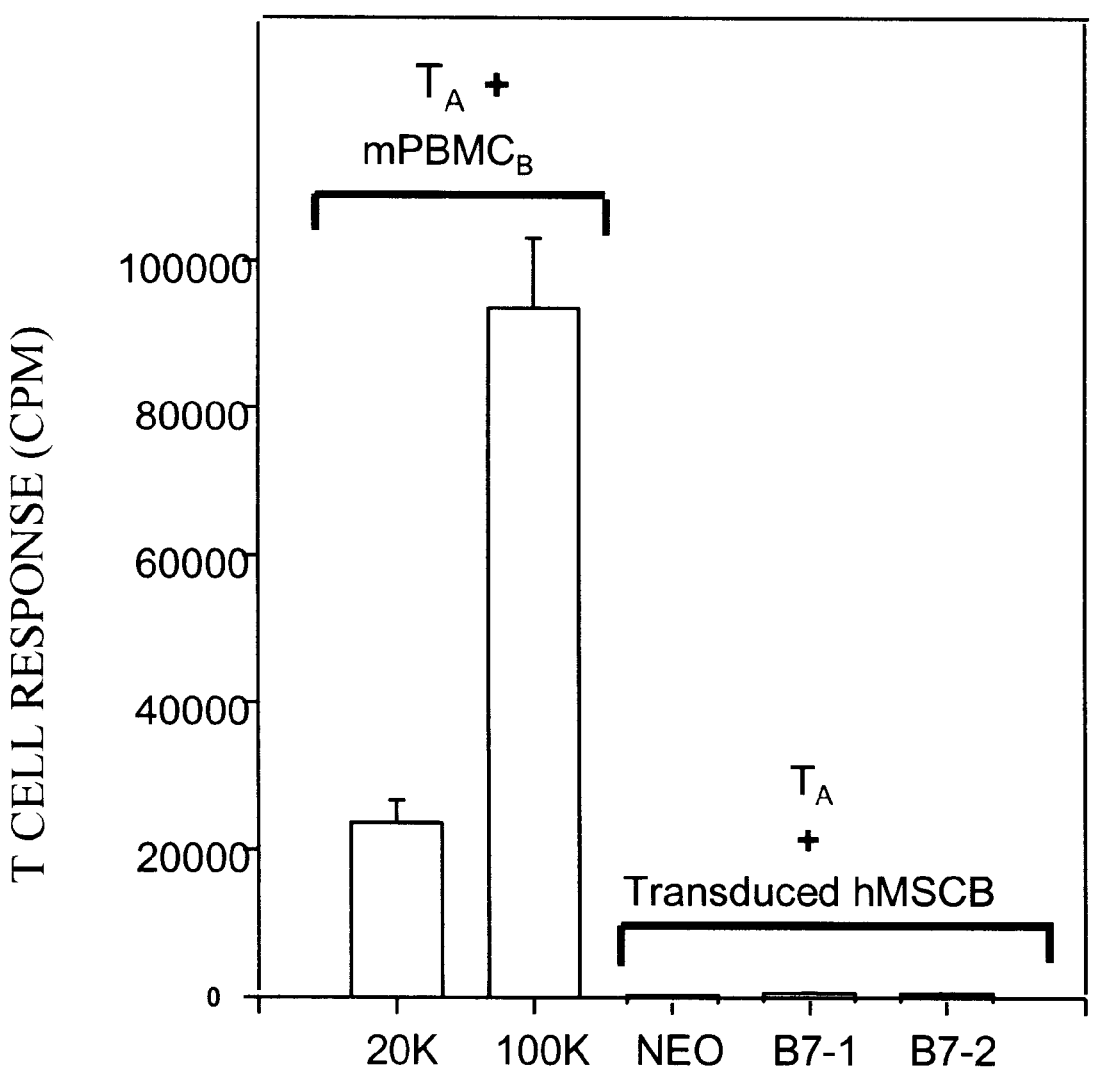
FIG. 1. The lack of alloreactivity to mesenchymal stem cells. T cells from A proliferated in a dose dependent manner when mixed with different amounts of PBMCs from B. T cells from A did not proliferate in response to contact with mesenchymal stem cells from B, even when the mesenchymal stem cells were manipulated to provide full T cell activation (the mesenchymal stem cells were transduced with costimulatory molecules B7-1 or B7-2).

Compositions according to the present invention which contain allogeneic mesenchymal stem cells are especially useful for facilitating repair, reconstruction and/or regeneration of a connective tissue defect. In accordance with one aspect of the present invention, the allogeneic mesenchymal stem cells can be employed in various methods and products for treating skeletal and other connective tissue disorders.

In another aspect, the present invention relates to various methods and devices for utilizing the allogeneic mesenchymal progenitor or stem cells in order to enhance hematopoietic cell production.

In a still further aspect of the invention described herein, allogeneic mesenchymal stem cells are genetically engineered (or transduced or transfected) with a gene of interest. The transduced cells can be administered to a patient in need thereof, for example to treat genetic disorders or diseases.

The methods and products of the invention utilize isolated and culture-expanded mesenchymal stem cells which are allogeneic to the recipient for whom they are intended. Although the invention is not limited thereby, mesenchymal stem cells can be isolated, purified, and expanded in culture, i.e. in vitro, to obtain sufficient numbers of cells for use in the methods described herein. See, Caplan and Haynesworth, U.S. Pat. No. 5,486,359; U.S. Pat. No. 5,197,985; U.S. Pat. No. 5,226,914; WO92/22584.

Thus in a preferred embodiment, the human mesenchymal stem cells are obtained from bone marrow taken from an individual allogeneic to the recipient. In a preferred embodiment, the mesenchymal cell preparation is substantially pure, i.e. is at least 95% free of allogeneic cells other than mesenchymal stem cells.

The subject human mesenchymal stem cells are obtained from the bone marrow or other mesenchymal stem cell source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood.

Isolated and purified allogeneic human mesenchymal stem cells can be grown in an undifferentiated state through mitotic expansion in a specific medium. These cells can then be harvested and activated to differentiate into bone, cartilage, and various other types of connective tissue by a number of factors, including mechanical, cellular, and biochemical stimuli. Human mesenchymal stem cells possess the potential to differentiate into cells such as osteoblasts and chondrocytes, which produce a wide variety of mesenchymal tissue cells, as well as tendon, ligament and dermis, and this potential is retained after isolation and for several population expansions in culture. Thus, by being able to isolate, purify, greatly multiply, and then activate mesenchymal stem cells to differentiate into the specific types of mesenchymal cells desired, such as skeletal and connective tissues such as bone, cartilage, tendon, ligament, muscle, adipose and marrow stroma, see U.S. Pat. No. 5,197,985, a highly effective process exists for treating skeletal and other connective tissue disorders.

Although in a preferred embodiment the mesenchymal stem cells are culturally expanded prior to use, it is also possible to use such mesenchymal stem cells without culture expansion. For example, mesenchymal stem cells may be derived from bone marrow and used after separation of blood cells therefrom, without expansion. Thus, for example, allogeneic bone marrow may be enriched in allogeneic human mesenchymal stem cells by removal of blood cells, and introduced into a patient in need thereof, e.g. for skeletal repair.

Thus, one embodiment of the present invention provides various methods and devices for enhancing the implantation and differentiation of allogeneic mesenchymal stem cells. Accordingly, the mesenchymal stem cells can be used for treatment of connective tissue disorders, for example to promote the growth of connective tissues. The term connective tissue is used herein to include the tissues of the body that support the specialized elements, and includes bone, cartilage, ligament, tendon, stroma, muscle and adipose tissue.

In accordance with a preferred aspect of this embodiment, the allogeneic mesenchymal stem cells can be employed in various methods and products for treating skeletal and other connective tissue disorders. The methods and devices of the invention utilize isolated allogeneic mesenchymal progenitor cells which, under certain conditions, can be induced to differentiate into and produce different types of desired connective tissue, such as into bone or cartilage forming cells.

In an additional aspect, the present invention is directed to various methods of utilizing human allogeneic mesenchymal stem or progenitor cells for therapeutic and/or diagnostic purposes. For example, allogeneic human mesenchymal stem or progenitor cells find use in: (1) regenerating mesenchymal tissues which have been damaged through acute injury, abnormal genetic expression or acquired disease; (2) treating a host with damaged mesenchymal tissue by treatment of damaged tissue with allogeneic mesenchymal stem cells combined with a biocompatible carrier suitable for delivering mesenchymal stem cells to the damaged tissues site(s); (3) producing various mesenchymal tissues; (4) detecting and evaluating growth factors relevant to mesenchymal stem cell self-regeneration and differentiation into committed mesenchymal lineages; (5) detecting and evaluating inhibitory factors which modulate mesenchymal stem cell commitment and differentiation into specific mesenchymal lineages; and (6) developing mesenchymal cell lineages and assaying for factors associated with mesenchymal tissue development.

The dose of the allogeneic mesenchymal stem cells varies within wide limits and will, of course be fitted to the individual requirements in each particular case. The number of cells used will depend on the weight and condition of the recipient and other variables known to those of skill in the art. The cells can be administered by a route which is suitable for the particular tissue or organ to be treated. The cells can be administered systemically, i.e., parenterally, by intravenous injection. In most cases, the allogeneic mesenchymal stem cells are delivered to the site of desired treatment or therapy and can be targeted to a particular tissue or organ, such as bone marrow.

The cells can be suspended in an appropriate diluent, at a concentration of from about 0.5 to about $5 \times 10^6$ cells/ml. Suitable excipients for such solutions are those that are biologically and physiologically compatible with the recipient, such as buffered saline solution. Other excipients include water, isotonic common salt solutions, alcohols, polyols, glycerine and vegetable oils. The composition for administration must be formulated, produced and stored according to standard methods complying with proper sterility and stability.

The human mesenchymal stem cells can be administered via a subcutaneous implantation of cells or by injection of stem cells, for example, into muscle cells.

In another aspect, the present invention relates to a method for repairing connective tissue damage. The method comprises the steps of applying an allogeneic mesenchymal stem or progenitor cell-containing extract to an area of connective tissue damage under conditions suitable for differentiating the cells into the type of connective tissue necessary for repair.

In a further embodiment of this aspect, the present invention is directed to a method for enhancing the implantation of a prosthetic device into skeletal tissue. The method comprises the steps of adhering allogeneic mesenchymal stem or progenitor cells onto the connective surface of a prosthetic device, and implanting the prosthetic device containing these mesenchymal cells under conditions suitable for differentiating the cells into the type of skeletal or connective tissue needed for implantation.

The invention provides a method for augmenting bone formation in an individual in need thereof. Thus, the methods of this aspect of the invention are applicable to "connective tissue defects" which include any damage or irregularity compared to normal connective tissue which may occur due to trauma, disease, age, birth defect, surgical intervention, etc. More particularly, the invention provides a method for effecting the repair of segmental bone defects, nonunions, malunions or delayed unions. As used herein, "connective tissue defects" also refers to non-damaged areas in which bone formation is solely desired, for example, for cosmetic augmentation. The methods and materials disclosed herein are therefore suitable for use in orthopedic, dental, oral, maxillofacial, periodontal and other surgical procedures.

The present invention is also directed to methods of utilizing the allogeneic mesenchymal progenitor or stem cells for correcting or modifying connective tissue disorders. Thus, in another aspect, the present invention is directed to various devices and factors that have been developed in order to induce the allogeneic mesenchymal stem or progenitor cells to differentiate into specific types of desired phenotypes, such as bone or cartilage forming cells. For example, the inventors have found that various porous tri-calcium or hydroxyapatite ceramic devices can be utilized as vehicles or carriers for the allogeneic mesenchymal stem or progenitor cells when implanted into skeletal defects thereby permitting and/or promoting the differentiation of the cells into skeletal tissue.

Thus, one embodiment of the invention is directed to a method for using a porous ceramic composition comprised of tri-calcium phosphate or hydroxyapatite or combinations of the two, as a vehicle or carrier for mesenchymal stem or progenitor cells, which when implanted into skeletal defects, promotes the differentiation of the cells into skeletal tissue.

In another embodiment, the invention is directed to a method for using absorbable gelatin, cellulose, and/or collagen-based matrix in combination with the allogeneic mesenchymal stem cells. This composition can be used in the form of a sponge, strip, powder, gel, web or other physical format.

Various alternative vehicles may be employed for delivery of human mesenchymal stem cells for repair of connective tissue. The compositions may be designed as a patch for the damaged tissue to provide bulk and scaffolding for new bone or cartilage formation. The various compositions, methods, and materials described herein can, in accordance with the present invention, be used to stimulate repair of fresh fractures, non-union fractures and to promote spinal fusion. See U.S. Pat. No. 5,197,985. Likewise, repair of cartilage and other musculoskeletal tissues can be accomplished. In the case of spinal fusion, such compositions, methods, and materials can be used posteriorly with or without instrumentation to promote mass fusion along the lamina and transverse processes and anteriorly, used to fill a fusion cage to promote interbody fusion. The methods of the present invention using allogeneic mesenchymal stem cells can be used to treat total joint replacement and osteoporosis.

In accordance with another aspect of the invention, the mesenchymal stem cells can be used to produce marrow stroma. The marrow stroma provides the scaffolding as well as soluble factors which direct and support blood cell synthesis, i.e., hematopoiesis. Accordingly, this aspect of the invention is directed to a method to improve the process of blood cell and marrow tissue regeneration in patients where the marrow is depleted or destroyed, such as, for example, during intensive radiation and chemotherapy treatment, by employing hematopoietic progenitor cells derived from, for example, bone marrow or peripheral blood.

Accordingly, in one embodiment, the present invention provides methods and products for using allogeneic mesenchymal stem cells to enhance engraftment of hematopoietic stem or progenitor cells.

Thus, one embodiment of the present invention provides a method for enhancing the regeneration of marrow tissue by using allogeneic mesenchymal stem cells. The method for enhancing hematopoietic stem or progenitor cell engraftment comprises administering to an individual in need thereof, (i) allogeneic mesenchymal stem cells and (ii) hematopoietic stem or progenitor cells, wherein said mesenchymal stem cells are administered in an amount effective to promote engraftment of such hematopoietic stem or progenitor cells in the individual. More particularly, one embodiment of the invention is directed to a method for using mesenchymal stem cells which, when administered systemically, will migrate, or home, to the marrow cavity and differentiate into marrow stroma, thereby regenerating the marrow stroma. The allogeneic mesenchymal stem cells can be administered systemically, e.g., intravenously, into various delivery sites or directly into the bone.

A further consideration in this aspect is directed to the timing of injection of the allogeneic mesenchymal stem cells into the patient relative to the administration of hematopoietic stem or progenitor cells. In one embodiment, the mesenchymal stem cells are injected simultaneously with the hematopoietic stem or progenitor cells. In another embodiment, the mesenchymal stem cells are administered before or after the administration of the hematopoietic stem or progenitor cells. The hematopoietic stem cells may be autologous or may be matched to the allogeneic cells.

The present invention is useful to enhance the effectiveness of bone marrow transplantation as a treatment for cancer. The treatment of cancer by x-irradiation or alkylating therapy destroys the bone marrow microenvironment as well as the hematopoietic stem cells. The current treatment is to transplant the patient after marrow ablation with bone marrow which has been previously harvested and cryopreserved. However, because the bone marrow microenvironment is destroyed, bone marrow engraftment is delayed until the stromal environment is restored. As a result, a critical aspect of the present invention is directed to the advantages of transplanting isolated, purified, culture-expanded allogeneic mesenchymal stem cells to accelerate the process of stromal reconstitution and regeneration of marrow tissue.

Modes of administration of the mesenchymal stem cell preparation include but are not limited to systemic intravenous injection and injection directly to the intended site of activity. The preparation can be administered by any convenient route, for example by infusion or bolus injection and can be administered together with other biologically active agents. Administration is preferably systemic.

In this aspect of the invention, the mesenchymal stem cell can be administered alone, however in a preferred embodiment, the mesenchymal stem cells are utilized in the form of pharmaceutical compositions. Such compositions comprise a therapeutically effective amount of the allogeneic mesenchymal stem cells, and a pharmaceutically acceptable carrier or excipient. Such a carrier includes but is not limited to saline, buffered saline, dextrose, water, and combinations thereof. The formulation should suit the mode of administration.

In a preferred embodiment, the mesenchymal stem cell preparation or composition is formulated in accordance with routine procedures as a pharmaceutical composition adapted for intravenous administration to human beings. Typically, compositions for intravenous administration are solutions in sterile isotonic aqueous buffer. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The method of the invention can be altered, particularly by (1) increasing or decreasing the time interval between injecting mesenchymal stem cells and implanting the tissue; (2) increasing or decreasing the amount of mesenchymal stem cells injected; (3) varying the number of mesenchymal stem cell injections; or (4) varying the method of delivery of mesenchymal stem cells.

The mesenchymal stem cell preparation is used in an amount effective to promote engraftment of hematopoietic stem or progenitor cells in the recipient. In general, such amount is at least $1\times10^4$ mesenchymal stem cell per kg of body weight and most generally need not be more than $3\times10^6$ mesenchymal stem cells/kg. Preferably, it is at least about $1\times10^6$ mesenchymal stem cells/kg prior to graft introduction and usually need not be more than about $2\times10^6$ mesenchymal stem cells/kg. The allogeneic mesenchymal stem cell preparation may be administered concurrently with the hematopoietic stem or progenitor cells or for a period prior to graft introduction of at least about 7 days but generally not to exceed 30 days, with a typical therapeutic treatment period of 7 to 14 days. The mesenchymal stem cell preparation preferably is administered either intravenously one to three times per day, and may be adjusted to meet optimal efficacy and pharmacological dosing.

The invention also provides a pharmaceutical pack or kit comprising one or more containers filled with one or more of the ingredients of the pharmaceutical preparation of the invention. Associated with such container(s) can be a notice in the form prescribed by a governmental agency regulating the manufacture, use or sale of pharmaceuticals or biological products, which notice reflects approval by the agency of manufacture, use or sale for human administration.

The present invention is particularly advantageous in that mesenchymal stem cells may be used for a variety of treatments wherein the source of the mesenchymal stem cells is other than the recipient and without requiring that such source be matched to the recipient. Moreover, such mesenchymal stem cells may be used without requiring chronic administration of immunosuppressants.

In a still further aspect, the present invention also is directed to the application of allogeneic human mesenchymal stem cells as genetically engineered cells that carry within them genes of interest particularly for the expression of physiologically or pharmacologically active proteins or for use in gene therapy.

In accordance with this aspect of the present invention, allogeneic human mesenchymal stem cells or progenitor cells can be used as host cells for the expression of exogenous gene products. These culture-expanded cells home to the marrow and enhance hematopoietic recovery in a marrow transplant setting. Furthermore, these cells can be manipulated for cellular therapy, e.g. expanded, purified, selected and maintained for clinical use while still maintaining their precursor phenotype. Part of this manipulation is the characterization of such cells and their cryopreservation for future use.

It is contemplated that the transformed allogeneic stem cells and the expression products of the incorporated genetic material can be used alone or in combination with other cells and/or compositions.

The technology used to introduce foreign genes into these progenitor cell cultures has been described, e.g. see U.S. Pat. No. 5,591,625, and provides transduced mesenchymal stem cells wherein all progeny of the cells carry the new genetic material. Cell delivery of the transformed cells can be effected through various modes including infusion and direct injection into periosteal, bone marrow, muscle and subcutaneous sites.

By virtue of this aspect of the present invention, genes can be introduced into allogeneic mesenchymal stem cells which are then administered to the patient where gene expression will effect its therapeutic benefit. Examples of such applications include genes that have a central role in mesenchymal cell maintenance, tissue development, remodeling, repair and in vivo production of extracellular gene products.

In addition to the correction of genetic disorders, this aspect of the present invention can introduce, in a targeted manner, additional copies of essential genes to allow augmented expression of certain gene products. These genes can be, for example, hormones, matrix proteins, cell membrane proteins cytokines, adhesion molecules, detoxification enzymes and "rebuilding" proteins important in tissue repair. Normal mesenchymal stern cells can be provided to treat abnormal mesenchymal stem cells.

An additional application is the use of introduced genes to alter the phenotype of the allogeneic mesenchymal stem cells and their differentiated progeny for specific therapeutic applications. This includes intracellular gene products, signal transduction molecules, cell surface proteins, extracellular gene expression products and hormone receptors. Disease states and procedures for which such treatments have application include genetic disorders of the musculoskeletal system, diseases of bone and cartilage, the bone marrow, inflammatory conditions, muscle degenerative diseases, malignancies and autologous or allogeneic bone or bone marrow transplantation.

In one embodiment, the isolated human mesenchymal stem cells are preferably mesenchymal stem cells that have been transformed with at least one DNA sequence capable of expressing those translation products capable of packaging a viral sequence so as to be gene therapy producer cells. In a preferred embodiment of this aspect, the isolated human mesenchymal stem cells have been transformed with a DNA sequence comprising a retroviral 5' LTR and, under the transcriptional control thereof, at least one of a retroviral gag, pol or env gene. In another aspect, the isolated human mesenchymal stem cells have also been transformed with a DNA sequence comprising a retroviral packaging signal sequence and incorporated genetic material to be expressed under the control of a promoter therefor so as to be incompetent retroviruses. Also contemplated is the transfection of mesenchymal stem cells or committed stromoblasts to initiate, modulate or augment hematopoiesis.

Virtually all genetic lesions of mesenchymal cells or tissue can be treated or "corrected" by this technology. A key component is the ability to deliver these gene-carrying stem cells to the proper tissue under the conditions that the stem cells will expand and repopulate the tissue space. Patient preparation for introduction of allogeneic mesenchymal stem cells includes, but is not limited to, (a) marrow ablation by chemotherapy and/or irradiation in conjunction with marrow transplantation, and (b) direct tissue infiltration of "transduced" cells without preparation, particularly where the transduced cells might have a survival advantage, an advantage during differentiation or an advantage in function (such as might be the case when correcting a muscle disorder such as muscular dystrophy with the dystrophin or similar gene). An additional application is in the tagging of mesenchymal stem cells prepared for use in vivo alone or as applied to any indwelling device, such as, for example, an orthopedic device in which it is of interest to "mark" the mesenchymal stem cell's and observe their survival, maintenance and differentiation and their association with the device over time.

The advantages provided by allogeneic human mesenchymal stem cells transfected with exogenous genetic material encoding a protein to be expressed include (a) the ability to utilize human mesenchymal stem cells obtained from a variety of sources other than the individual into which they will be administered, i.e., allogeneic to the individual; (b) the ability to deliver these gene-carrying mesenchymal stem cells to the proper tissue in a patient without inducing an adverse immune response, thus minimizing the need for immunosuppressive therapy prior to administration of the cells; (c) the ability to culturally expand human mesenchymal stem cells for infusion where they will localize to mesenchymal tissue spaces; (d) the ability to culturally expand and cryopreserve human mesenchymal stem cells which can be used as hosts for stable, heritable gene transfer; (e) the ability to recover genetically altered cells after installation in vivo; (f) the ability to match a genetic therapy to a wide variety of disorders, pinpointing the genetic alteration to the target tissue; and (g) the ability of newly introduced genes within human mesenchymal stem cells and their progeny to be expressed in a less restrictive fashion than other cells, thereby expanding the potential application in treating medical disease.

The structure and life cycle of retroviruses makes them ideally suited to be gene-transfer vehicles. Generally regarding retroviral mediated gene transfer, see McLachlin et al., *Progress in Nucleic Acid Research and Molecular Biology*, 38:91–135 (1990). Transformation of stem cells using retroviruses has been described in U.S. Pat. No. 5,591,625.

It is also possible to use vehicles other than retroviruses to genetically engineer or modify the allogeneic stem cells. Genetic information of interest can be introduced by means of any virus which can express the new genetic material in such cells, for example, SV40, herpes virus, adenovirus and human papillomavirus. Many methods can be used for introducing cloned eukaryotic DNAs into cultured mammalian cells, which include transfection mediated by either calcium phosphate or DEAE-dextran, protoplast fusion and electroporation. The genetic material to be transferred to stem cells may be in the form of viral nucleic acids, bacterial plasmids or episomes.

The present invention makes it possible to genetically engineer allogeneic mesenchymal human stem cells in such a manner that they produce polypeptides, hormones and proteins not normally produced in human stem cells in biologically significant amounts or produced in small amounts but in situations in which overproduction would lead to a therapeutic benefit. These products would then be secreted into the bloodstream or other areas of the body, such as the central nervous system. The human stem cells formed in this way can serve as a continuous drug delivery systems to replace present regimens, which require periodic administration (by ingestion, injection, depot infusion etc.) of the needed substance. This invention has applicability in providing hormones, enzymes and drugs to humans, in need of such substances. It is particularly valuable in providing such substances, such as hormones (e.g., parathyroid hormone, insulin), which are needed in sustained doses for extended periods of time.

For example, it can be used to provide continuous delivery of insulin, and, as a result, there would be no need for daily injections of insulin. Genetically engineered human mesenchymal stem cells can also be used for the production of clotting factors such as Factor VIII, or for continuous delivery of dystrophin to muscle cells for muscular dystrophy.

Incorporation of genetic material of interest into allogeneic human mesenchymal stem cells is particularly valuable in the treatment of inherited and acquired disease. In the case of inherited diseases, this approach is used to provide genetically modified human mesenchymal stem cells and other cells which can be used as a metabolic sink. That is, such human mesenchymal stem cells would serve to degrade a potentially toxic substance. For example, this could be used in treating disorders of amino acid catabolism including the hyperphenylalaninemias, due to a defect in phenylalanine hydroxylase; the homocysteinemias, due to a defect in cystathionine β-synthase. Other disorders that could be treated in this way include disorders of amino acid metabolism, such as cystinosis; disorders of membrane transport, such as histidinurea or familial hypocholesterolemia; and disorders of nucleic acid metabolism, such as hereditary orotic aciduria.

Allogeneic human mesenchymal stem cells of the present invention can also be used in the treatment of genetic diseases in which a product (e.g., an enzyme or hormone) normally produced by the body is not produced or is made in insufficient quantities. Here, human mesenchymal stem cells transduced with a gene encoding the missing or inadequately produced substance can be used to produce it in sufficient quantities. This can be used in producing alpha-1 antitrypsin. It can also be used in the production of Factor XIII and Factor IX and thus would be useful in treating hemophilia.

There are many acquired diseases for which treatment can be provided through the use of engineered allogeneic human mesenchymal stem cells (i.e., human mesenchymal stem cells transduced with genetic material of interest). For example, such cells can be used in treating anemia, which is commonly present in chronic disease and often associated with chronic renal failure (e.g., in hemodialysis patients). In this case, human mesenchymal stem cells having incorporated in them a gene encoding erythropoietin would correct the anemia by stimulating the bone marrow to increase erythropoiesis (i.e. production of red blood cells). Other encoded cytokines can be G-CSF or GM-CSF, for example.

The allogeneic human mesenchymal stem cells of the present invention can also be used to administer a low dose of tissue plasminogen activator as an activator to prevent the formation of thrombi. In this case, human mesenchymal stem cells having incorporated genetic material which encodes TPA would be placed into an individual in whom thrombus prevention is desired. This would be useful, for example, as a prophylactic against common disorders such as coronary artery disease, cerebrovascular disease, peripheral vascular occlusive disease, vein (e.g., superficial) thrombosis, such as seen in pulmonary emboli, or deep vein thrombosis. Human mesenchymal stem cells which contain DNA encoding calcitonin can be used in the treatment of Paget's Disease, a progressive, chronic disorder of bone metabolism, in which calcitonin is presently administered subcutaneously.

Another application is a subcutaneous implantation of allogeneic human mesenchymal stem cells alone or adhered to a porous ceramic cube device which will house the mesenchymal stem cells and allow them to differentiate in vivo. Another example would be injection of allogeneic mesenchymal stem cells into muscle where they will differentiate into muscle cells. Another example might be a graft having genetically engineered human mesenchymal stem cells which continuously secrete a polypeptide hormone, e.g. luteinizing hormone-releasing hormone (LHRH) for use in birth control.

Human mesenchymal stem cells engineered to produce and secrete interleukins (e.g., IL-1, IL-2, IL-3 or IL-4 through IL-11) can be used in several contexts. For example, administration of IL-3 through human mesenchymal stem cells which contain genetic material encoding IL-3 can be used to increase neutrophil count to treat neutriopenia. Allogeneic human mesenchymal stem cells can also be transduced with the gene for thrombopoietin and when administered to an individual having a condition marked by a low platelet count, production and secretion of the encoded product will result in stimulation of platelet production.

Another use of the present invention is in the treatment of enzyme defect diseases. In this case the product (polypeptide) encoded by the gene introduced into human mesenchymal stem cells is not secreted (as are hormones); rather, it is an enzyme which remains inside the cell. There are numerous cases of genetic diseases in which an individual lacks a particular enzyme and is not able to metabolize various amino acids or other metabolites. The correct genes for these enzymes could be introduced into the allogeneic mesenchymal stem cells and transplanted into the individual; the transplant would then carry out that metabolic function. For example, there is a genetic disease in which those affected lack the enzyme adenosine deaminase. This enzyme is involved in the degradation of purines to uric acid. It is believed possible, using the present invention, to produce a subcutaneous graft as described above capable of producing the missing enzyme at sufficiently high levels to detoxify the blood as it passes through the area to which the graft is applied.

Additional uses include but are not limited to cytokine genes to enhance hematopoietic reconstitution following marrow transplantation for bone marrow failure for congenital disorders of the marrow; bone cytokines to improve repair and healing of injured bone; bone matrix problems to improve repair and healing of injured or degenerative bone; correction of mesenchymal genetic disorders such as osteogenic imperfecta and muscular dystrophy; localized production of proteins, hormones etc. providing cellular therapeutics for many different compounds; and cytotoxic genes such as thymidine kinase which sensitizes cells to ganciclovir. Gap junction adhesion to tumor cells could allow mesenchymal stem cells to serve for cancer therapy.

It is to be understood, however, that the scope of the present invention is not to be limited to the specific embodiments described above. The invention may be practiced other than as particularly described and still be within the scope of the accompanying claims.

It should be understood that the methods described herein may be carried out in a number of ways that are well known in the art, with numerous modifications and variations thereof. It may also be appreciated that any theories set forth as to modes of action or interactions between cell types should not be construed as limiting this invention in any manner, but are presented such that the methods of the invention can be more fully understood.

The following examples further illustrate aspects of the present invention. However, they are in no way a limitation of the teachings or disclosure of the present invention as set forth herein.

EXAMPLE 1

Lack of Alloreactivity to Mesenchymal Stem Cells

Cell surface antigens responsible for eliciting transplant rejection are class I and class II MHC antigens. T cells are alloreactive to foreign MHC antigens. Class I and II MHC molecules stimulate the mixed lymphocyte reaction.

$1 \times 10^5$ T cells from individual A ($T_A$) were cultured in flat bottom microtiter wells with mitomycin C treated allogeneic PBMCs (to prevent proliferation of PBMCs to T cells) from individual B (mPBMC$_B$) for 7 days. The mPBMC$_B$s were seeded at 20K and 100K. The cultures were pulsed with $^3$H-thymidine for the last 18 hours of the culture period to measure T cell proliferation. The results shown in FIG. 1 indicate that the $T_A$ cells recognized the PBMC$_B$ as being foreign. (See bars under "$T_A$+mPBMC$_B$".) With more PBMC$_B$s present, the more the T cells proliferated.

$2 \times 10^4$ human mesenchymal stem cells (hMSCs) from the same donor as the PBMCs were co-incubated with $1 \times 10^5$ T cells from individual A ($T_A$). The cells were cultured in flat-bottom microtiter wells for a total of 7 days. Cultures were pulsed with $^3$H-thymidine for the last 18 hours of the culture period to measure T cell proliferation. Two days prior to coculture with the T cells, the human mesenchymal stem cells were seeded into microtiter wells at the number given above (confluent) and treated with IFN-γ (50 units/ml) to stimulate surface MHC expression on mesenchymal stem cells. Human mesenchymal stem cells or human mesenchymal stem cells transduced with human B7–1 or human B7–2 costimulation molecules (Lafferty, K. J., Prowse, S. J., and C. J. Simeonovic. *Ann. Rev. Immunol.* 1:143–73 (1983)) were incubated with the T cells.

The results shown in FIG. 1 (See FIG. 1 "$T_A$+transduced hMSCs") demonstrate that the T lymphocytes were nonresponsive (did not proliferate) to the human mesenchymal stem cells transduced or untransduced, i.e., they were not recognized as being foreign. Thus, there was no mixed lymphocyte reaction.

The results also show that the lack of response to the mesenchymal stem cells was not due to genetic compatibility between the individuals since the T cells did recognize peripheral blood mononuclear cells (PBMC$_B$) from the mesenchymal stem cell donor as being foreign.

EXAMPLE 2

Suppression of Mixed Lymphocyte Reaction

To determine whether mesenchymal stem cells actively suppressed the allogeneic response, mixed lymphocyte reactions (MLR) were set up in tissue culture plates, with or without adherent mesenchymal stem cells obtained from 2 different donors: one donor matched the target or stimulator cell in the MLR and the other donor was unrelated.

$10^5$ PBMCs from individual A (PBMC$_A$) were mixed with $10^5$ target individual B's PBMC's (PBMC$_B$). The PBMC$_B$S were irradiated (stimulator cells) with 3000 rads X irradiation to prevent their proliferation due to activation by PBMC$_A$s. Thus, only PBMC$_A$s proliferated (responder cells). When PBMC$_A$s and PBMC$_B$s were mixed, a mixed lymphocyte reaction occurred wherein the PBMC$_A$ cells were activated by the surface antigens on the PBMC$_B$s. The cultures were incubated over an interval of 7 days and were pulsed with $^3$H-thymidine during the final 18 hours. In the presence of the PBMC$_B$s, the PBMC$_A$s proliferated giving counts of 40,000. See FIG. 2, 1st bar, ("NONE" refers to no mesenchymal stem cells present).

However, when PBMC$_A$s and PBMC$_B$s were mixed in the presence of mesenchymal stem cells, the mixed lymphocyte reaction was suppressed. $10^5$ PBMC$_A$s were mixed with $10^5$ PBMC$_B$s in microtiter plate wells coated with a monolayer of human mesenchymal stem cells. The mesenchymal stem cells were plated in the wells in amounts ranging from 7500 to 22,500 mesenchymal stem cells per well. Two mesenchymal stem cell populations were tested: human mesenchymal stem cells were obtained from an individual that matched individual B's MHC type and human mesenchymal stem cells were obtained from an individual that did not match either individual A's or B's MHC type. The cultures were incubated over an interval of 7 days and were pulsed with $^3$H-thymidine during the final 18 hours. In the presence of the human mesenchymal stem cells, the MLR was suppressed. See FIG. 2. Thus, regardless of the MHC origin of the mesenchymal stem cells, the mesenchymal stem cells suppressed the mixed lymphocyte reaction.

Figure 2:
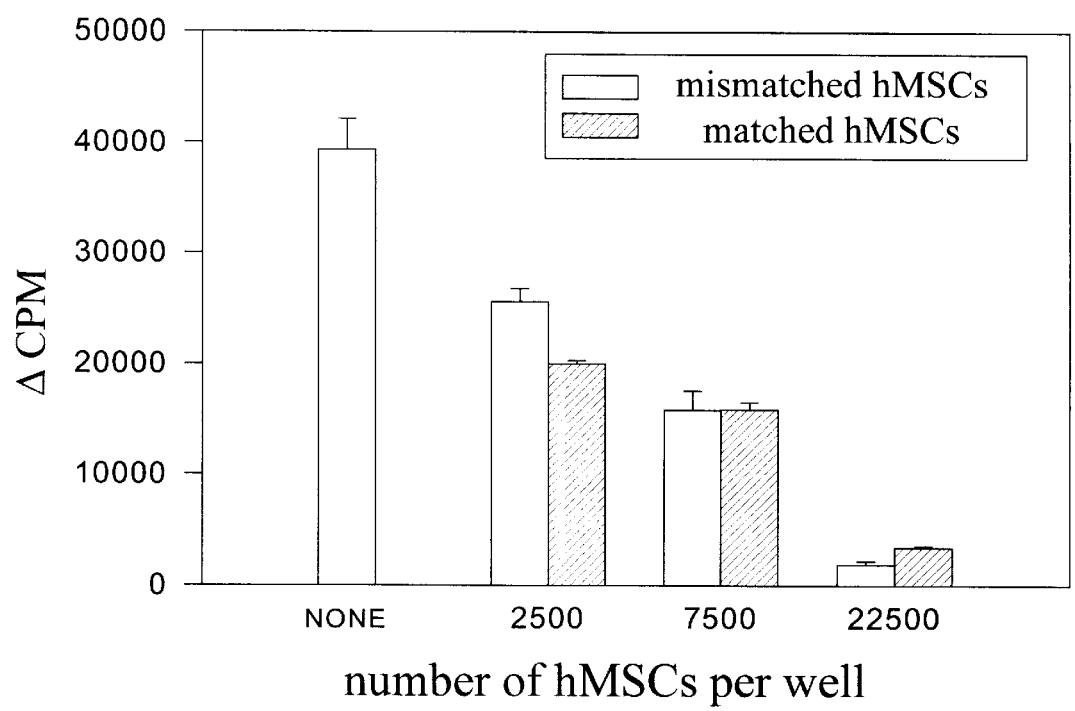
FIG. 2. Mesenchymal stem cells actively suppressed the mixed lymphocyte reaction between lymphocytes from two different individuals. hMSC-1 was a third party to both the stimulator and responder cells in the mixed lymphocyte reaction; hMSC-2 was autologous to the stimulator cells in the mixed lymphocyte reaction. Thus, the mesenchymal stem cells suppressed the mixed lymphocyte reaction without specificity as to MHC type. The mesenchymal stem cells suppressed the mixed lymphocyte reaction in a dose dependent manner.
Figure 3A:
FIG. 3A–3E. Allogeneic canine study. Histological analysis 6 week autologous sample processed in DMEM-LG showed a substantial amount of bone.
Figure 3B:
Figure 3C:
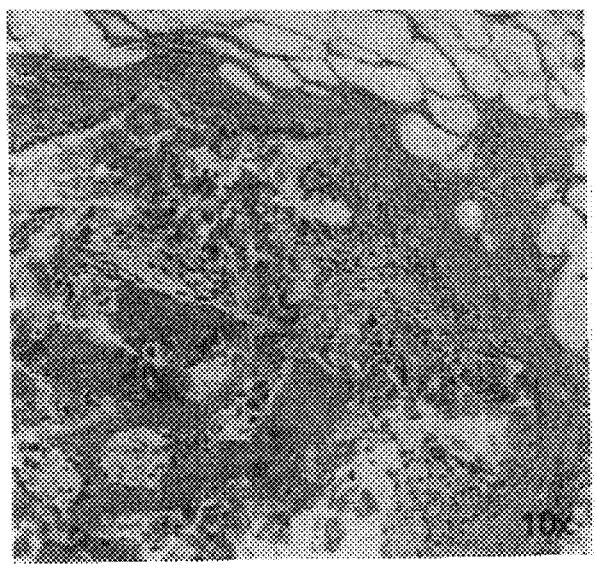
Figure 3D:
Figure 3E:
Figure 4A:
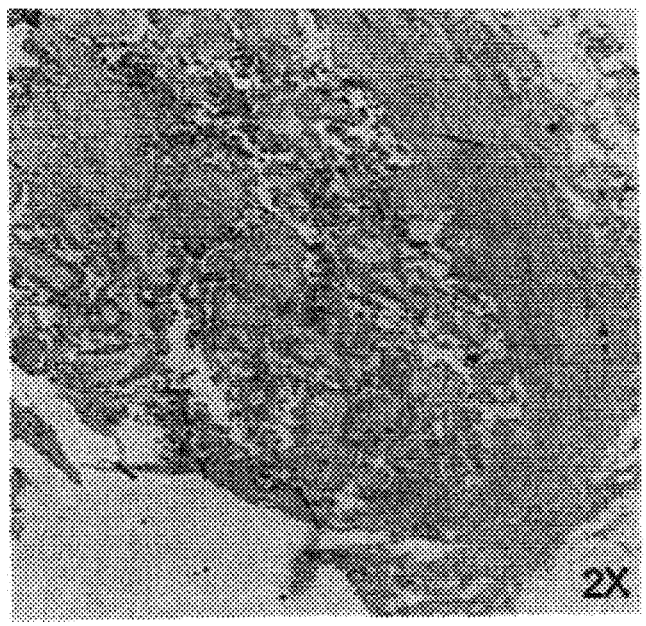
FIG. 4A–4E. Allogeneic canine study. Histological analysis of 6 week allogenic sample showed bone formation.
Figure 4B:
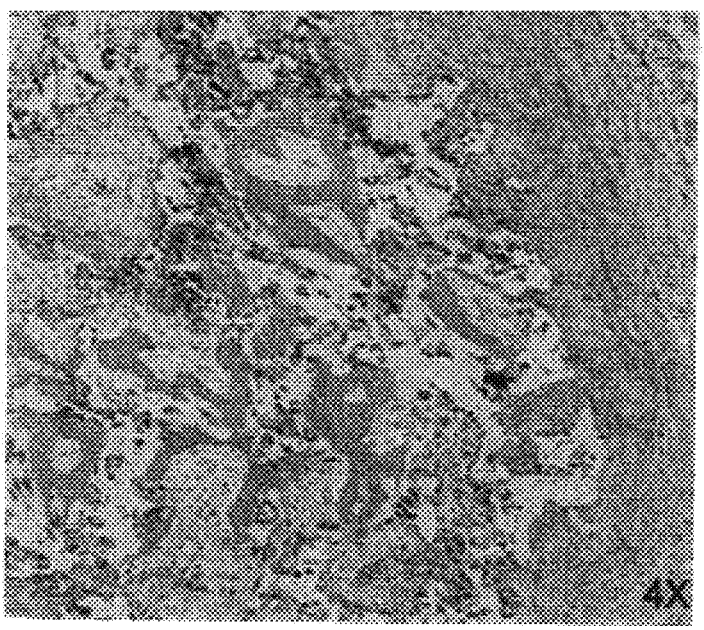
Figure 4C:
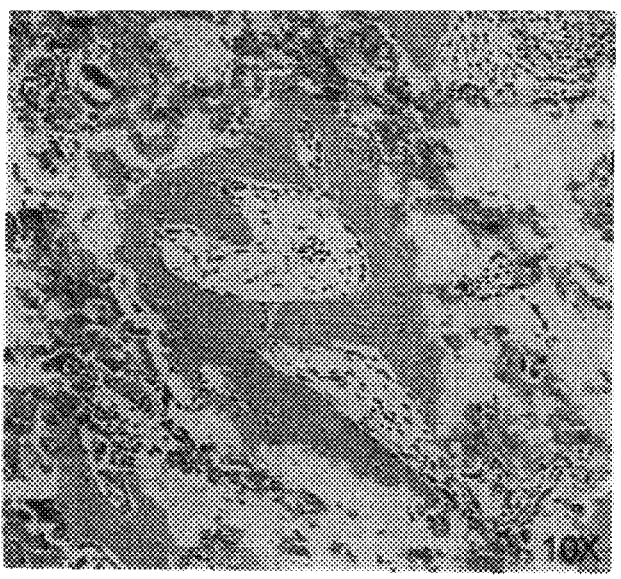
Figure 4D:
Figure 4E:
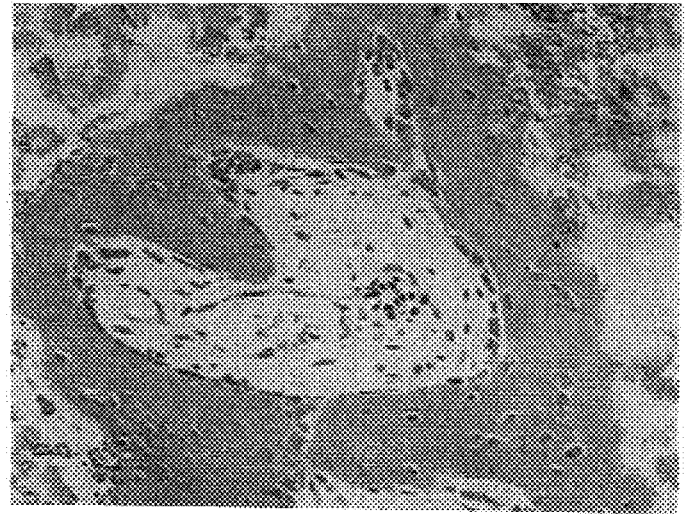
Figure 5A:
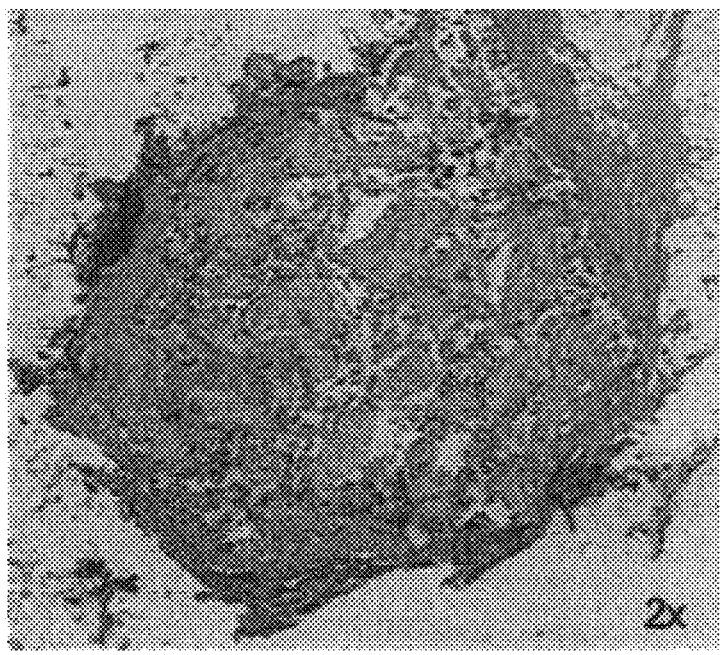
FIG. 5A–5D. Allogeneic canine study. Histological analysis 6 week allogenic sample from different donor than that shown in FIG. 4 also showed bone formation.
Figure 5B:
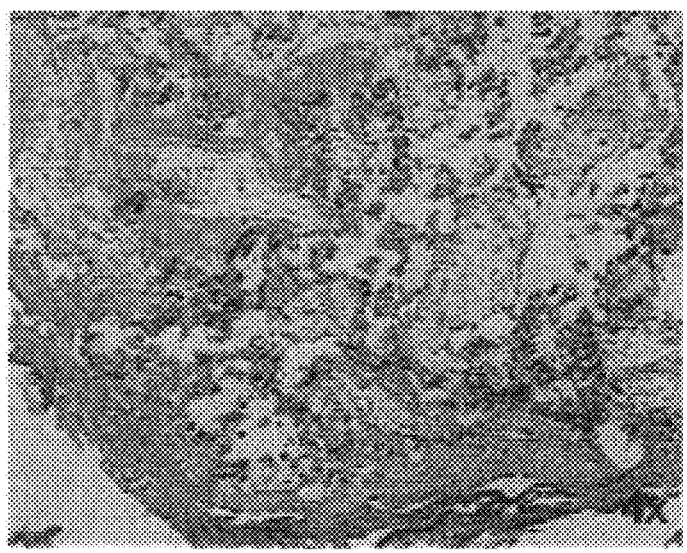
Figure 5C:
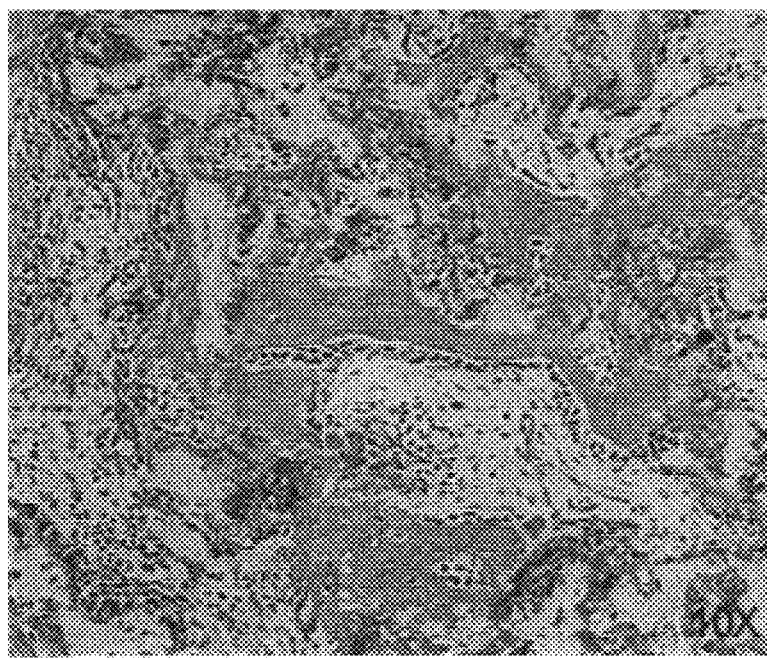
Figure 5D:
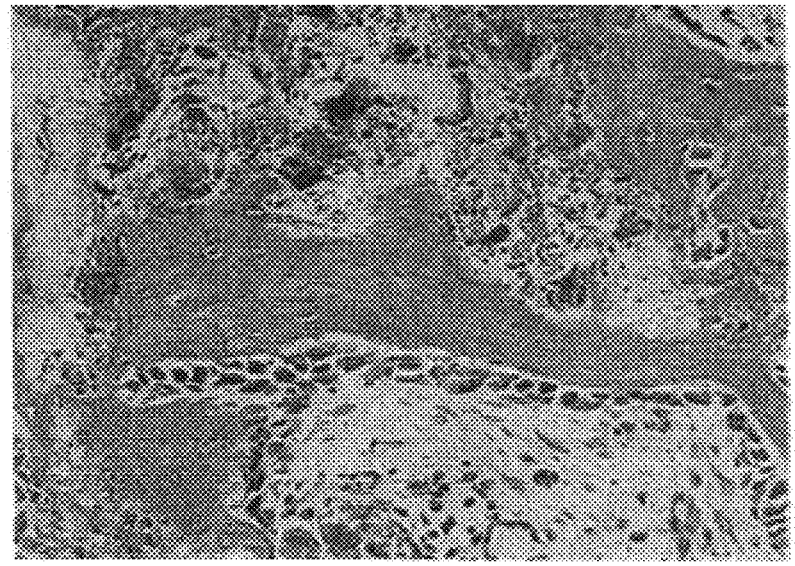

The results shown in FIG. 2 also indicate that the human mesenchymal stem cells decreased the mixed lymphocyte reaction in a dose-dependent manner. Mesenchymal stem cells from either donor suppressed proliferation equally well, which indicated that there was no specificity of suppression with respect to MHC type. These results demonstrate that mesenchymal stem cells actively suppressed the mixed lymphocyte reaction when the cells were cultured together.

EXAMPLE 3

Allogenic Canine Subcutaneous Study

The purpose of this study was to determine whether implantation of allogenic MSC-loaded HA/TCP samples subcutaneously resulted in an immune response in canines and whether this response had an effect on MSC-mediated osteogenesis.

Two canines were used for this allo-subcutaneous implantation. Each canine received 6 autogeneic MSC-implants in one thigh and 3 allogeneic from each of two allogeneic donors in the contralateral thigh. Three of the autogeneic implants and all the allo-samples were loaded in serum-free phenol-free DMEM-low glucose. The other three autogeneic samples were loaded in serum-free DMEM-high glucose. Only cryo-preserved MSCs were used in the study and the samples were loaded 24 hours prior to implantation.

Two samples of each type were assigned for histological processing and one for RNA extraction. In addition, limited amount of blood and lymph nodes were collected for determination of immune response. The end points were 2 weeks and 6 weeks. The 2 week canine had bilateral tendon surgery, whereas the 6 week canine had unilateral tendon surgery on the limb that received the autogeneic subcutaneous implants. The canines in the study were not littermates.

Results

Gross observations of the implant bed at sacrifice and also general health observation did not indicate any major immune reaction to the allo-implants at either the 2 week or 6 week end point. The popliteal lymph nodes were enlarged in both limbs at both time points. The inguinal lymph nodes could not be identified. Preliminary MLR data using PBMCs from one combination of the donor-host pair indicated a positive reaction with a count of 15K in the proliferation assay indicating that this pair is mismatched.

The two week histological section from the auto and allo-samples were indistinguishable from each other. There was loose connective present in all samples and no bone formation was seen in any of the samples (as expected at 2 weeks). Histological data was obtained from one sample out of two of each group at the 6 week time point. The 6 week autologous sample processed in the DMEM-LG had a substantial amount of bone in the sample (FIG. 3). The allo-sample from each of the two allo-donors was also positive for bone (FIGS. 4 & 5) and the pattern of tissue formation was similar to that of the auto-sample. The amount of bone formation in allo-samples was lower than in auto-sample. However, given the variability in the amount of bone formation associated with this assay, no conclusion can be drawn on the basis on the limited sample size. No immune response could be observed in any of the allo-samples under H&E stain.

The bone formation data in these preliminary studies clearly shows that canine MSCs retain their osteogenic potential in an allogeneic setting and do not elicit a major immune response.

EXAMPLE 4

The purpose of the study was to demonstrate the feasibility and safety in dogs of the infusion of a moderately high dose of donor dog leukocyte antigen (DLA)-identical littermate canine mesenchymal stem cell (cMSC) at $10 \times 10^6$ cells/kg in an allogeneic marrow graft setting. A secondary objective was to examine the distribution and function of donor neo- and GFP-marked cMSC at 50 and 100 days post-transplant.

MATERIALS AND METHODS

Experimental Animals

Beagles were used for the study. Two male and two female DLA-identical littermates were used in the study, aged 7 or 9 months on day 0. The method for typing used involves the use of highly polymorphic microsatellite markers to follow inheritance of the Class II DRB region in the Dog Leukocyte Antigen (DLA), the canine equivalent of the major histocompatability complex. Microsatellites are small di- tri- or tetra nucleotide repeats, which show sufficient length variation in alleles that they may be used to follow the inheritance of chromosomal segments through multigeneration crosses. Segregation of alleles is typically monitored using a single-step polymerase chain reaction with primers derived from unique sequences of DNA that surround each repeat. In addition, mixed leukocyte reactions were performed on the DLA-identical littermate pairs chosen for study to provide confirmation of the PCR microsatellite marker assay results.

Study Design

The dogs underwent transplantation with cMSC and bone marrow from the same DLA-identical littermate donor. The marrow graft was harvested from each of the two DLA-identical littermates on day 0 prior to total body irradiation (TBI) and exchanged. Myeloablation was induced by exposing the dogs on day 0 to a single TBI dose of 920 centigray (cGy) (midline air exposure from two opposing $^{60}$Co sources delivered at a rate of 7 cGy (9.3 R)/min. Culture-expanded cMSC isolated from a donor marrow aspirate at 4 or more weeks prior to transplantation, were transduced with Papp@OT-24, containing the genes for green fluorescence protein (GFP) and neomycin phosphotransferase (neo). The cMSC were cryopreserved after passage 1 (P1) or passage 2 (P2). Following TBI, the cMSC were thawed and delivered intravenously via a portable infusion pump over a 15-minute time period. Within one to two hours after cMSC infusion the bone marrow graft was infused intravenously at a dose of $\geq 1 \times 10^8$ total nucleated cell (TNC)/kg.

Cyclosporin was administered to all four dogs for graft-versus-host-disease (GVHD) prophylaxis intravenously on days 0 through 5 at a dose of 10 mg/kg BID (20 mg/kg/day) (Sandimmune® Injection Solution, Novartis Pharmaceuticals Corporation). On days 6 through 50 (end of study) for group I.1.a, or 6 through 100 for group I.1.b, cyclosporin was administered at 10 mg/kg BID PO, (20 mg/kg/day) (Neoral® Soft Gelatin Capsules, Novartis Pharmaceuticals Corporation). The usual supportive care with oral antibiotics for the recipient began on day −5 and systemic antibiotics started on day 0 and continued until engraftment was achieved. Fluid support was given as necessary. No platelet transfusions were required for any of the four dogs during recovery. Standard canine procedures require that a whole blood transfusion be administered if the platelet count consistently drops below 10,000/mm$^3$, or if the treatment staff observes signs of bleeding. Platelet transfusions, if necessary, were to be administered as 50-ml of whole irradiated (2000 cGy) blood from a random donor. Engraftment was established as the time of the first of three consecutive measurements of >500 absolute neutrophil cells mm$^3$, >1,000/mm$^3$, and platelets >10,000/mm$^3$, 50,000/mm$^3$, and >100,000.

To follow hematopoietic recovery, complete blood counts (CBCs) were obtained from day 0 through day 50, and biweekly thereafter for the 100-day study group. Serum chemistry analysis was performed on days 0, 2, and weekly thereafter. Peripheral blood samples were taken on day 0 pre-MSC infusion, 5- and 15-minutes, 1- and 2-hours, and 1-, 2-, 3-, and 4-day time points for DNA isolation. The DNA was evaluated for the presence of GFP marked cells by an Anti-EGFP DNA PCR Elisa with digoxigenin incorporated into the product and a second step anti-digoxigenin calorimetric assay. A marrow aspirate was obtained when the platelet counts consistently reached 50,000/mm$^3$ and examined for the presence of GFP marked cells using the same PCR method. CMSC cultures were established to examine colony forming units (CFU), and to expand the cMSC for further Anti-EGFP PCR analysis. Upon necropsy, peripheral blood, bone marrow aspirates, and bone marrow biopsies were obtained for Anti-EGFP PCR analysis. CFU assays were performed on the bone marrow aspirates, and the Anti-EGFP PCR analysis was performed on culture-expanded cMSC. An histological analysis was performed for the presence of GFP in various tissues.

cMSC Isolation, Culture-expansion, Transduction and Cryopreservation

Bilateral bone marrow aspirates were obtained for cMSC isolation and culture establishment on week −4 for dogs CAN-07-01 and CAN-07-02 and on week −9 for dogs CAN-07–03 and CAN-07-04. Fifteen ml of marrow (7 ml from each humerus) were obtained from each dog. Dogs were anesthetized by the injection of Butorphanol followed by injection of a mixture of Diazepam and ketamine hydrochloride (Aveco Co., Inc., Fort Dodge, Iowa). The sites of needle insertion were scrubbed with povidone-iodine and then rinsed with alcohol. Aspirates were obtained from each humeral condyle of each dog using a 16-gauge, 2-inch bone marrow needle. A syringe was attached to the needle, and suction was applied to remove 8 ml of marrow from each humerus. Bone marrow aspirates were transferred to 15 ml polypropylene conical tubes using sterile technique. Following the procedure, the dog was then placed on a warming pad to recover.

Five to 10 ml aliquots of bone marrow were diluted to 50 ml in Dulbecco's Phosphate Buffered Saline (DPBS) in a polypropylene culture tube. The cell suspensions underwent centrifugation at 2200 RPM for 10 minutes at room temperature (RT). Total nucleated cell counts were determined in 4% acetic acid. Cells were then diluted in DPBS for a final concentration of $20 \times 10^6$ cells/ml. Ten ml or $200 \times 10^6$ cells were loaded onto 20 ml of Percoll (sp.gr. 1.073 gm/ml) in a 50 ml conical tube and underwent centrifugation at 1300 RPM for 20 minutes. The cell interface containing mononuclear cells was washed in DPBS, resuspended in complete media, and counted to obtain a recovery percentage. The cells were then diluted in complete media, cultures were established as described below, and placed in a 37° C. incubator at 5% $CO_2$.

Construction of Bicistronic MuL V Retroviral Vector

Figure 6:
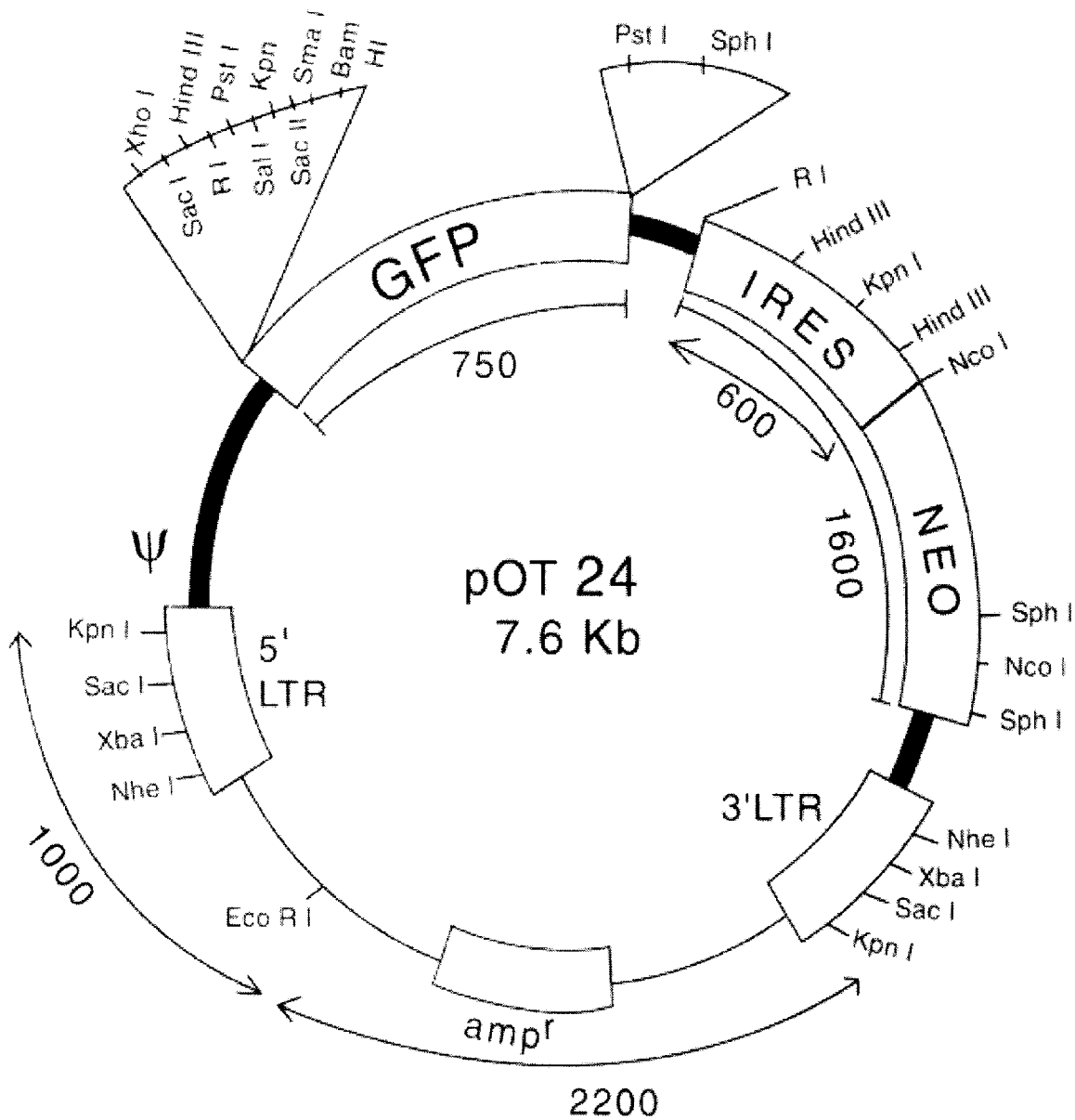
FIG. 6. A schematic map of EGFP pOT24 plasmid used in Example 4.

The green fluorescent protein (EGFP) retrovirus was constructed by isolating EGFP-1 gene from the jellyfish Aequorea Victoria (Clontech, Calif.). EGFP gene was cloned into retroviral vector pJM573-neo (resulting plasmid was named pOT-24). The plasmid pJM573-neo was derived from pN2 (Keller et. Al., 1985, *Nature* 318:149) with the following modifications: murine retroviral gag initiation site was substituted with an in-frame stop codon; 5'LTR and 3'LTR were constructed into the same cassette; neomycin phosphotransferase gene (neo) and an internal ribosomal entry site (IRES) were inserted into pN2. A schematic map of EGFP pOT24 plasmid is shown in FIG. 6.

Preparation of Recombinant Retrovirus pOT-24 was transfected into GP&E86 ecotropic producer cells using DOTAP (Boehringer Manheim) as suggested by manufacturer. The transfected cells were grown in DMEM-high glucose (HG) medium supplemented with 10% heat inactivated FBS, Penicillin-Streptomycin (Life Technologies) and 0.5 mg/ml of protamine sulfate-G418 (Sigma) as a selective marker. Cultures were maintained up to 70% confluency at which point medium was replaced with fresh retroviral media (without G418) and cells were maintained at 32° C. for 2 days. The culture medium containing the retrovirus was collected, filtered through $0.45\mu$ filter and stored at −70° C. Amphotropic retrovirus was prepared by transducing PA317 cells twice with ecotropic virus using a centrifugal transduction procedure followed by selection with G418 (0.5 mg/ml). Retroviral supernatant was collected. The titer of the pooled EGFP retrovirus on 3 T3 cells was $1.2 \times 10^6$ CFU/ml. GFP-retroviral supernatants were cryopreserved at −70° C.

CAN-07-01 and CAN-07-02

The washed mononuclear cells obtained at the Percoll interface were established in 10, T185 flasks containing 30 ml of complete media and $10 \times 10^6$ cells/flask.

On days 2, 6, and 9 of culture, the media in the flasks was replaced entirely with fresh complete media. On day 12 of the primary culture photographs were taken, and the cells were taken from passage 0 (P0) to passage 1 (P1). The media was aspirated and the flasks were washed twice with 8 ml DPBS. Eight ml of trypsin was added, and flasks were placed in a 37° C. incubator for 3 minutes. When the cells had lifted, the reaction was stopped by the addition of 8 ml of complete media. The cells were transferred and pooled into 50 ml conical tubes. The flasks were washed with DPBS and the pooled cells were centrifuged at RT at 2000 RPM for 5 minutes. The supernatant was removed and the cell pellets were resuspended in complete media. The cells were pooled, counted and examined for viability. Cells were plated into 15, T80 flasks containing 18 ml of complete medium and $0.4 \times 10^6$ cells per flask.

On day 15 in culture, the first transduction was performed on 15 of the 18 flasks. The media was removed. Aliquots of the retroviral supernatant were thawed and polybrene was added to a final concentration of 8 $\mu$g/ml to make the transduction cocktail. The cell medium was replaced with 10 ml of the transduction cocktail, and the flasks were centrifuged at 3000 RPM for 1 hour at 32° C. After centrifugation, 10 ml of complete media prepared using heat inactivated fetal bovine serum (FBS) was added to each flask (with the transduction cocktail) and the flasks were returned to the incubator. Three flasks were not transduced, and fresh media was replaced. On day 16 of culture, the media was replaced with fresh complete media. On day 17 of culture the transduction procedure was repeated.

On day 18 of culture, the cells were harvested as described above and taken from P1 to P2. Three$\times 10^6$ cells were added to 100 ml of complete medium, and poured into triple-flasks (500 cm$^2$). Fifteen triple-flasks were prepared with transduced cells and three were prepared with untransduced cells. Any remaining cells were cryopreserved. A freeze solution was prepared containing 10% DMSO and 90% FBS. Ten$\times 10^6$ cells were resuspended in 1 ml of freezing solution. The vials were labeled and cryopreserved in a Nalgene Cryo container for a minimum of 4 hours at −70° C., and stored at −70° C.

On day 22 of P2 culture, photographs were taken to record the cell distribution and morphology and the P2 cells were harvested and cryopreserved as described below.

CAN-07-03 and CAN-07-04

The washed mononuclear cells obtained at the Percoll interface were established in 15, T75 flasks containing 20 ml of complete media and $12\times10^6$ cells/flask.

On day 2 of culture, the media in the flasks and in the dishes was replaced entirely with fresh complete media. On day 6 of primary culture for cMSC, the first transduction was performed as described above. Three flasks were not transduced, and fresh media was replaced on day 6. On day 7 of culture, the media was replaced with fresh media.

On day 8 of culture the transduction procedure was repeated. On day 9 in culture, photographs were taken, and the cells were passaged from P0 to P1 as described above. Three$\times10^6$ cells were added to 100 ml of complete medium, and poured into triple flasks. Fifteen triple-flasks were prepared with transduced cells and three were prepared with untransduced cells.

The 15 ml bone marrow aspirates yielded 910, 1212, 856, and $1948\times10^6$ nucleated cells for donors CAN-07-01, CAN-07-02, CAN-07-03, and CAN-07-04, respectively. Mononuclear cell counts obtained from the Percoll interface were 612, 666, 588, and $462\times10^6$, resulting in recoveries of 67.2, 55, 68.7, and 23.7%. Upon PI, the cell viability was a mean of 97.1 (range 93.3 to 100)%. Upon P2 for donors CAN-07-01 and CAN-07-02, and P1 cells for donors CAN-07-03 and CAN-07-04, the cell viability of the transduced cells was a mean of 96.7 (range 96.3 to 97.9)%. The untransduced cells were 95.4 (range 93.3 to 96.9)% viable. Upon harvest for cryopreservation of the cMSC, the viability of the transduced cells was a mean of 99.4 (range 97.4 to 100)% and the untransduced cells were 99.4 (range 97.6 to 100)% viable (Table 4).

The transduced cMSC yield per flask for donors CAN-07-01 and CAN-07-02, harvested 4 days after passage 2 and plated at $3\times10^6$ per flask was 5.9 and $6.7\times10^6$, and the untransduced cMSC yield per flask was 8.4 and $7.5\times10^6$. The transduced cMSC yield per flask for donors CAN-07-03 and CAN-07-04, harvested 4 days after passage 1 (different transduction and passage design) and plated at $3\times10^6$ per flask was 20.0 and $14.0\times10^6$, and the untransduced cMSC yield per flask was 25.3 and $18.0\times10^6$.

CFU Assays on cMSC from P0 Cultures

CFU colony assays were prepared at the time of primary culture establishment by plating $0.5\times10^6$ cells in triplicate in 100 mm dishes containing 10 ml complete media. The dishes were incubated at 37° C. and 5% $CO_2$. The media was replaced with fresh media each 2 to 4 days. On day 10 in culture, the CFU assay dishes were rinsed with HBSS twice, fixed with 1% gluteraldehyde for 15 minutes, rinsed with HBSS twice, and air dried. The cMSC in the dishes were then stained with 0.1% crystal violet, rinsed with deionized water three times, and air dried. Colonies were counted to calculate the number of colonies forming per $10^6$ cells plated.

CFU assays plated on day of mononuclear cell isolation and culture establishment and harvested on day 10 yielded 56, 46.7, 114, and 72 colonies per $10^6$ cells for dogs CAN-07-01, CAN-07-02, CAN-07-03, and CAN-07-04, respectively.

On day 13 of P1 culture, photographs were taken to record the cell distribution and morphology and the P1 cells were harvested by trypsinization and cryopreserved as described below.

The media in the triple flasks was decanted, and the flasks were rinsed with 50 ml DPBS. After decanting the DPBS, 23 ml of 0.25% trypsin was added to each triple flask. The flasks were placed in a 37° C. incubator for 3 minutes. After cell detachment, 23 ml complete medium was added to each flask. The cell suspensions were transferred to 50 ml conical tubes and the flasks were washed with 30 ml HBSS. The tubes were centrifuged at 2200 RPM for 5 minutes at RT. The pellets containing the transduced or untransduced cells, respectively, were pooled and counted. One aliquot of $1\times10^7$ cells was set aside for determination of the transduction percentage by an Anti-EGFP DNA PCR Elisa assay.

After harvest, the recovered P1 or P2 transduced and culture-expanded cMSCs centrifuged at 1300 RPM for 5 minutes and resuspended in 1 ml aliquots with $1\times10^7$ cMSC/ml in ice-cold cryoprotectant solution containing 85% Plasma-Lyte A (Baxter IV Therapy), 10% DMSO, and 5% autologous canine serum. Cell aliquots were dispensed into separate cryo-vials containing 1 ml each. The tubes were labeled with the canine donor number and total viable cell count. The cMSCs were cryopreserved by placing the cell vials into a Nalgene freezing container and placed in a −70° C. freezer for 4 hours, then moved to storage at −70° C.

Upon cell harvest for cryopreservation of the product, aliquots of $1\times10^7$ cells were obtained for determination of the transduction efficiency. The transduction efficiency was analyzed by an Anti EGFP DNA PCR Elisa with digoxigenin incorporation into the product and a second step Anti-digoxigenin calorimetric assay.

CMSC Infusion Product

One to two hours before infusion, the vials of cMSC were thawed by swirling in a 37° water bath, sprayed with 70% ethanol, and opened in a biosafety cabinet. The cMSC product was suspended in 50 ml of infusion medium containing DMEM-LG plus 30% serum autologous to the cell donor. The viability of the cMSC product was determined by exclusion of trypan blue to determine the actual viable dose. An aliquot of each cMSC product was submitted for yeast isolate, aerobic, and non-aerobic growth. The cMSCs were evaluated for the ability to attach to tissue culture plastic and to proliferate in P2 (P3 for CAN-07-01 and CAN-07-02) culture. Aliquots of $1\times10^6$ and $0.16\times10^6$ cMSC were plated into complete canine culture medium in triplicate in T-25 plastic culture flasks. After 24 hours, the flasks plated with $1\times10^6$ cMSC and on day three, the flasks plated with $0.16\times10^6$ cMSC were harvested by trypsinization and counted.

Following TBI, the cMSC suspension was infused via a catheter inserted into the cephalic vein using a hand-held Harvard Bard Mini Infuser to deliver the 50 ml over a 15–20 minute period.

Moderately high doses of 7.49, 7.35, 10.0, and 10.0 (mean 8.7)$\times10^6$ viable cMSC/kg were infused on day 0 to dogs CAN-07-01, CAN-07-02, CAN-07-03, and CAN-07-04, respectively. These doses represent a 4- to 10-fold increase over the typical dose that a patient would receive. Total viable cMSC infused ranged from 67.7 to 129 (mean 93.9)$\times 10^6$ cMSC. The viability of the cells ranged from 92.1 to 97.6 (mean 94.9) as determined by trypan blue exclusion. CMSC Infusions were given between 71 and 146 (mean 110) minutes post-TBI.

Blood Sampling Post-Infusion

Blood samples (2 ml) were obtained before (pre) and during the cMSC infusion at five and fifteen minutes after the start of the infusion, as well as 1- and 2-hour, and 1-, 2-, 3-, and 4-day time points. Cell lysates were prepared using the Puregene™ (Gentra Systems, Inc.) DNA Isolation Kit for use in an Anti EGFP DNA PCR Elisa with digoxigenin incorporated into the product and a second step Anti-digoxigenin colorimetric assay to detect of the level of GFP marked cMSC in the bloodstream.

Bone Marrow Harvest and Graft Infusion

Bone marrow to be used as the transplant graft was harvested from the DLA-identical littermate prior to TBI. Aspirates were obtained from each humerus using an 11-gauge, 4–6 inch ball-top stainless steel marrow harvest needle, attached to polyvinyl tubing originating from a vacuum flask containing 100 ml Tissue Culture Medium 199 and 4 ml (4000 U) heparin. The marrow is passed through 300- and 200-um pore size, and stored at 4° C. in a transfer pack container, labeled with the donor and recipient, until infusion later that day. The bone marrow total nucleated cell count (BM-TNC) of the marrow is corrected to exclude any nucleated cells which would be present in the volume of peripheral blood obtained during the marrow harvest.

The total nucleated cell count (TNC) of the bone marrow was corrected to exclude any TNC which would be present in the volume of peripheral blood obtained during the marrow harvest. Corrected doses of marrow were 4.3, 3.5, 3.1, and 2.0 (mean 3.2)$\times 10^8$ TNC/kg to dogs CAN-07-01, CAN-07-02, CAN-07-03, and CAN-07-04, respectively. Uncorrected bone marrow doses were 5.6, 4.2, 4.5, and 2.7 (mean 4.3)$\times 10^8$ TNC/kg.

Twenty minutes prior to infusion, the marrow was placed at room temperature. One hour after the cMSC infusion, the marrow was infused intravenously through a butterfly needle inserted into the cephalic vein, by exerting pressure on the bag over 1 to 2 minutes.

Supportive Care

On day −5, oral antibiotics (neomycin sulfate and polymyxin sulfate) were given three times daily. These oral antibiotics were administered until absolute neutrophil counts reached 500/mm$^3$. On day 0, the systemic antibiotic Baytril was administered intravenously twice daily and continued until absolute neutrophil counts reached 1,000/mm$^3$ consistently. Fluid and electrolytes lost as results of transient radiation toxicity were replaced by subcutaneous administration of 500 ml of Ringers Solution, twice daily until food and water were accepted.

Differential Blood Cell Counts

Blood samples (2 ml) were collected from either the jugular or cephalic vein on the mornings of the marrow aspirate for isolation of cMSC, days 0 through 50 and biweekly thereafter through the end of study. The blood was transferred into a vacutainer containing EDTA. Total white blood cell (WBC) and platelet counts per mm$^3$ are measured using a Sysmex E2500 and differential cell counts were determined manually after fixation and staining with Wrights stain.

Necropsy

Blood samples were obtained for CBC, Chemistry 23 analysis, and PCR evaluation. The dogs were sedated with Butorphanol followed by a mixture of Diazepan and ketamine hydrochloride. After sedation, biopsies and bilateral bone marrow aspirates were obtained from the humerii, femora, and iliac crests. Euthanasia was then completed with an overdose of the sedative sodium pentobarbital. The day-50 group of dogs (CAN-07-01 and CAN-07-02) were euthanised on day 43 in the study; the day-100 group of dogs (CAN-07-03 and CAN-07-04) were euthanised on day 100 in the study. Complete sets of the tissues were collected upon necropsy of the animals.

The collection of tissues for histological examination followed immediately. A subset of tissues was used for Anti-EGFP DNA PCR Elisa analysis. Bone marrow aspirates and biopsies were used for Anti-EGFP DNA PCR Elisa analysis, culture expansion for further PCR analysis, and CFU assays The tissues were trimmed to about 1 inch square pieces and placed into separate labeled 50 ml conical tubes filled with 10% Neutral Buffered Formalin (pH 6.8–7.2). The tissues were embedded in paraffin, sectioned and stained with Hematoxylin and Eosin. Bone marrow samples were stained with Periodic Acid Schiff's stain.

Bone marrow aspirates obtained prior to necropsy were collected in 15 ml labeled tubes from the left and right humerii, femora, and iliac crests from each dog. A subset of the tissue samples were obtained during necropsy and trimmed to about ¼ inch square pieces, wrapped in PBS-soaked gauze and placed separately in a labeled zip-lock bag. The bone marrow aspirates were held on ice.

Preparation of Bone Marrow Aspirates for CFU Assay

Aliquots of the bone marrow aspirates from the left and right humerus, femur, and iliac crest from each canine obtained for PCR analysis were aliquoted into separate 15 ml labeled tubes. The bone marrow samples were held on ice.

CFU Assay on cMSC From Bone Marrow Obtained at Necropsy

CFU colony assays performed on cMSC obtained from bone marrow obtained at necropsy were prepared by plating $0.5 \times 10^6$ cells in triplicate in 100-mm dishes containing 10 ml complete media. The dishes were incubated at 37° C. and 5% $CO_2$. The media was replaced with fresh media each 2–4 days. On day 10 in culture, the CFU assay dishes were rinsed with HBSS twice, fixed with 1% gluteraldehyde for 15 minutes, rinsed with HBSS twice, and air dried. The cMSC in the dishes were then stained with 0.1% crystal violet, rinsed with deionized water three times, and air dried. Colonies were counted to calculate the number of colonies per $10^6$ cells plated.

Isolation and Purification of DNA

DNA was isolated from a part of each tissue. The remaining piece of the sample was cryopreserved and stored in −70° C. freezer. DNA was isolated by placing samples in Phosphate Buffered Saline (PBS), adding proteinase K solution, and incubating at 55° C. for 3 hrs, or until the tissue dissolved. The samples were subsequently treated with RNase at 37° C. for 60 min. The samples were cooled to room temperature and the protein was precipitated. The samples were centrifuged and the aqueous phase was gently collected in 100% isopropanol. The samples were mixed and centrifuged and the pellet was washed in 70% ethanol. The tubes were centrifuged and the supernatant was drained off and the pellets were allowed to dry for approximately 1 to 6 hrs. The DNA was allowed to hydrate overnight at room temperature and was subsequently stored at 4° C.

Peripheral blood and bone marrow samples were first lysed with RBC lysis solution (Ammonium Chloride Buffer). DNA was then isolated from the lysates as described above. DNA was quantified by the addition of 998 $\mu$l deionized $H_2O$ and 2 $\mu$l DNA from the sample into a cuvette and vortexed. A spectrophotometer was used to determine the optical density (OD). The OD was read at 260 and 280, and the concentration of DNA was calculated for $\mu$g/ml. The DNA concentration was adjusted to 1 $\mu$g/ml using deionized water.

Anti-EGFP DNA PCR Elisa

The anti-EGFP DNA PCR Elisa assay used in these studies detects infused cMSCs utilizing oligonucleotide primers specific for GFP. For analysis of gene expression, we utilized PCR-ELISA (DIG labeling/detection) kit (Boehringer Mannheim). Briefly, PCR was performed in the presence of digoxigenin-labeled nucleotides to label the amplified product. Next, 25 $\mu$l of the PCR product was denatured and allowed to hybridize in solution to 5'-biotinylated oligonucleotide probe at 37° C. in streptavidin-coated microtiter plate. The bound probe-PCR product was detected by an anti-digoxigenin peroxidase conjugate and by use of the colorimetric substrate 2,2'Azinobis (3-ethylbenzthiazoline-sulfonic Acid) (ABTS). Titration standard curves were generated using transfected control CMSC to approximate concentration of DNA per quantity of DNA used in the assay. By first correlating with an internal standard for PCR of the DLA Class II genomic DNA, and then correlating DNA concentration to cell equivalents, and assuming one retrovirus integration event per transduced cell, an estimation of cell number can be obtained.

Quantitative measurements of DNA for GFP were noted in all bone marrow scoops/biopsies.

Post-transplant Blood Cell Recovery

The mean day to a threshold (to 3 consecutive values) of platelets to 10,000/mm$^3$ was 12.8 (range 11–17), to 50,000/mm$^3$ was 19.8 (range 16–25), and to 100,000/mm$^3$ 23.0 (range 20–27) The mean day to a threshold value (to 3 consecutive days) of absolute neutrophil cells to 500/mm$^3$ was 9.3 (range 8–11), and to 1,000/mm$^3$ was 10.5 (range 9–13).

Interim Bone Marrow Aspirates

When platelets recovered consistently to values greater than 50,000 per mm$^3$, an interim bone marrow aspirate was collected from the iliac crest. This procedure was performed on day 27 in study for CAN-07-01 and CAN-07-02, and on day 29 for CAN-07-03 and CAN-07-04.

RESULTS

Upon histopathological evaluation of all tissues from CAN-07-01 and CAN-07-02, euthanised on day 43, findings were negative for ectopic connective tissue and for subacute GVHD.

Detectable DNA signal could be found within 1 hour of infusion and again at 2 days. One sample could be quantitatively measured at 3 days post infusion for GFP DNA. This timepoint is consistent with the previous observations in the autologous canine transplant study in which signal was found at 2 and 3 days Day 100 necropsy data in CAN-07-03 and CAN-07-04 for GFP+ cells showed GFP signal (1 GFP+ cell equivalent per 10 micrograms PCR input DNA) in the femur and humerus of CAN-07-03 and in the humerus of CAN-07-04.

These results demonstrate that allogeneic MSCs can support the rapid engraftment of bone marrow hematopoietic cells. No transfusion support was needed. There was no clinical evidence of GvHD. Platelet recovery was faster than in historical controls. There was evidence of chimerism in stromal cells after allogeneic transplantation. The option to engraft allogeneic tissue by using allogeneic MSCs broadens the range of transplant material usable in clinical transplant scenarios.

What is claimed is:

1. A method for treating a human subject for promoting connective tissue growth, comprising:

treating a recipient human subject in need of connective tissue growth by administering a therapeutically effective amount of allogeneic mesenchymal stem cells to said recipient human subject, wherein said allogeneic mesenchymal stem cells are obtained from a donor human subject and wherein a step of MHC matching of said donor human subject to said recipient human subject is not employed prior to the administration of said allogeneic mesenchymal stem cells to the recipient human subject.

2. The method of claim 1 wherein the allogeneic human mesenchymal stem cells are recovered from human bone marrow and are administered to the recipient human subject in a cell preparation which is substantially free of blood cells.

3. The method of claim 2 wherein the cell preparation is administered in conjunction with a carrier for the cell preparation.

4. The method of claim 1 wherein the allogeneic mesenchymal stem cells are administered to generate bone formation.

5. The method of claim 1 wherein the allogeneic human mesenchymal stem cells are administered to treat or repair a connective tissue defect in the recepient human subject.

6. The method of claim 5 wherein the defect is a bone defect.

7. The method of claim 5 wherein the defect is a cartilage defect.

8. The method of claim 5 wherein the defect is a skeletal tissue defect.

9. The method of claim 5 wherein the allogeneic human mesenchymal stem cells are administered.

10. The method of claim 1 wherein the allogeneic human mesenchymal stem cells are administered systemically.

11. The method of claim 1 wherein the preparation is administered intravenously.

12. The method of claim 1 wherein the allogeneic human mesenchymal stem cells express incorporated genetic material of interest.

* * * * *

UNITED STATES PATENT AND TRADEMARK OFFICE
CERTIFICATE OF CORRECTION

PATENT NO.   : 6,355,239 B1
DATED        : March 12, 2002
INVENTOR(S)  : Scott P. Bruder It is certified that error appears in the above-identified patent and that said Letters Patent is hereby corrected as shown below:

Column 16,
Line 19, delete "3 T3" and insert therefor -- 3T3 --

Column 17,
Line 42, delete "cMSCfrom" and insert therefor -- cMSC from --

Column 21,
Line 8, delete "CMSC" and insert therefor -- cMSC --

Column 22,
Line 41, after "administered" insert -- for growth of stroma. --

Signed and Sealed this

Eleventh Day of March, 2003

JAMES E. ROGAN
*Director of the United States Patent and Trademark Office*